(12) United States Patent
Wright et al.

(10) Patent No.: US 7,109,168 B1
(45) Date of Patent: Sep. 19, 2006

(54) RETRO-INVERSO PEPTIDES DERIVED FROM LEUKEMIA INHIBITORY FACTOR

(75) Inventors: David E. Wright, Ramona, CA (US); D. Elliott Parks, Del Mar, CA (US)

(73) Assignee: Myelos Corporation, Iselin, NJ (US)

( * ) Notice: Subject to any disclaimer, the term of this patent is extended or adjusted under 35 U.S.C. 154(b) by 631 days.

(21) Appl. No.: 10/048,307

(22) PCT Filed: Jun. 16, 2000

(86) PCT No.: PCT/US00/16760

§ 371 (c)(1),
(2), (4) Date: May 7, 2002

(87) PCT Pub. No.: WO00/77029

PCT Pub. Date: Dec. 21, 2000

(51) Int. Cl.
*A61K 38/16* (2006.01)
*C07K 7/08* (2006.01)
*C07K 14/00* (2006.01)
*C07K 1/00* (2006.01)

(52) U.S. Cl. ............... 514/13; 514/2; 514/12; 530/300; 530/324; 530/325; 530/326

(58) Field of Classification Search ............ None
See application file for complete search history.

(56) References Cited

U.S. PATENT DOCUMENTS 4,698,327 A * 10/1987 Nagarajan et al. ............ 514/8
5,376,544 A * 12/1994 Lazarus et al. ............ 435/190
5,700,909 A * 12/1997 O'Brien ........................ 530/326
5,843,892 A * 12/1998 Patterson ........................ 514/12
6,217,871 B1 * 4/2001 Rose et al. ............ 424/184.1
6,586,403 B1 * 7/2003 Mathison et al. ............ 514/18

FOREIGN PATENT DOCUMENTS

WO       WO 9839357 A1 * 9/1998

OTHER PUBLICATIONS

Y. Takahama, et al. Oncogene (1998) 16, pp. 3189-3196.*
J. Rudinger. In: Peptide Hormones, JA Parsons, Ed. (1976) 1-7.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
W.S. Messer, "Vasopressin and Oxytocin", web document updated Apr. 3, 2000; <http://www.neurosci.pharm.utoledo.edu/MBC3320/vasopressin.htm>; 5 pages.*
S. Rudikoff, et al. Proc. Natl. Acad. Sci. USA (1982) 79, pp. 1979-1983.*

* cited by examiner

*Primary Examiner*—Bruce R. Campell
*Assistant Examiner*—Andrew D. Kosar
(74) *Attorney, Agent, or Firm*—Kenyon & Kenyon LLP

(57) ABSTRACT

Retro-inverso peptides derived from leukemia inhibitory factor (LIF) having between 18 and about 40 amino acids and including the sequence shown in SEQ ID NO: 1. These peptides have the same activity as native LIF and also have neurotrophic activity. Because of the D-amino acid linkage in the peptides, they are less susceptible to proteolytic degradation in vivo.

9 Claims, No Drawings

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: peptide derived from human LIF

<400> SEQUENCE: 1

Tyr Thr Ala Gln Gly Glu Pro Phe Pro Asn Asn Val Glu Lys Leu Cys
1               5                   10                  15

Ala Pro
```

RETRO-INVERSO PEPTIDES DERIVED FROM LEUKEMIA INHIBITORY FACTOR

FIELD OF THE INVENTION

The present invention relates to retro-inverso peptides derived from leukemia inhibitory factor (LIF). These peptides have activities similar to that of the native parent protein, and also have neurotrophic activity.

BACKGROUND OF THE INVENTION

Cytokines are proteins which are produced during the effector phases of natural and specific immunity and serve to mediate and regulate immune and inflammatory responses. Cytokines, like other polypeptide hormones, initiate their action by binding to specific receptors on the surface of target cells. One of the most well known families of cytokines are the interleukins which mediate natural immunity. For a detailed description of the structure and function of the interleukins, see Abbas et al. *Cellular and Molecular Immunology*, W. B. Saunders Company, Philadelphia, pp. 225–243, 1991.

Leukemia inhibitory factor (LIF), named for its ability to inhibit proliferation of a myeloid leukemic cell line by inducing differentiation, is a member of a family of ligands that includes IL-6, oncostatin M, ciliary neurotrophic factor (CNTF) and cardiotrophin-1 (Gearing, *Adv. Immunol.* 53:31–58, 1993; Pennica et al., *J. Biol Chem.* 270:10915–10922, 1995; Patterson, *Proc. Natl. Acad. Sci. U.S.A.* 91:7833–7835, 1994). Although these cytokines share only very limited sequence homology, they exert very similar effects on a variety of tissues. For example, several of these proteins, including LIF, can induce the same set of acute-phase response proteins in liver, support the self renewal of cultured embryonic stem cells, inhibit lipogenesis and enhance the survival of cultured motor neurons. LIF is produced by diverse cell populations, including macrophages, synoviocytes and chondrocytes. When applied to peripheral nerves in vivo, LIF is retrogradely transported and rescues damaged sensory neurons (Hendry et al., *J. Neurosci.* 12:3427–3434, 1992; Cheema et al., *J. Neurosci. Res.* 37:213–218, 1994). LIF also regulates the growth and differentiation of osteablasts and endothelial cells. The rising follicular fluid LIF level around the time of ovulation indicates that LIF may play a role in ovulatory events, early embryonic development and implantation (Senturk et al., *Am. J. Reprod. Immunol.* 39:144–151, 1998; Stewart, *Annals N.Y. Acad. Sci.* 157–165).

Neurotrophins and neurotrophic factors are proteins or peptides capable of affecting the survival, target innervation and/or function of neuronal cell populations (Barde, *Neuron*, 2:1525–1534, 1989). The efficacy of neurotrophins both in vivo and in vitro has been well documented. For example, ciliary neurotrophic factor (CNTF) promotes survival of chicken embryo ciliary ganglia in vitro and supports survival of cultured sympathetic, sensory and spinal motor neurons (Ip et al., *J. Physiol. Paris,* 85:123–130, 1991).

A major obstacle to the in vivo therapeutic use of peptides is their susceptibility to proteolytic degradation. Retro-inverso peptides are isomers of linear peptides in which the direction of the sequence is reversed (retro) and the chirality, D or L, of each amino acid is inverted (inverso). There are also partially modified retro-inverso isomers of linear peptides in which only some of the peptide bonds are reversed and the chirality of the amino acid residues in the reversed portion is inverted. The major advantage of such peptides is their enhanced activity in vivo due to improved resistance to proteolytic degradation (For review, see Chorev et al., *Trends Biotech.,* 13:438–445, 1995). Although such retro-inverso analogs exhibit increased metabolic stability, their biological activity is often greatly compromised (Guichard et al., *Proc. Natl. Acad. Sci U.S.A.,* 91:9765–9769, 1994). For example, Richman et al. (*J. Peptide Protein Res.,* 25:648–662) determined that analogs of linear and cyclic leu-enkephalin modified at the Gly$^3$—Phe$^4$ amide bond had activities ranging from 6%–14% of native leu-enkephalin. Chorev et al., (ibid.) showed that retro-inversion of a peptide which inhibits binding of vitronectin to its receptor resulted in one peptide which was less potent than the parent isomer by a factor of 50,000, and another peptide which was 4,000 fold more potent than the parent cyclic peptide. Guichard et al. (*TIBTECH* 14, 1996), teach that retro-inverso (all-D-retro) antigenic mimicry may only occur with peptides in random coil, loop or cyclic conformations. In the case of "helical" peptide, adequate functional mimicry would be expected only if the helicity was, in fact, absent under the solvent conditions used for assessing antigenic mimicry.

There is a need for LIF-derived and neurotrophic peptides exhibiting increased metabolic stability while retaining biological activity. The present invention addresses this need.

SUMMARY OF THE INVENTION

One embodiment of the present invention is an isolated retro-inverso peptide having between 18 and about 40 amino acids, wherein said peptide includes the sequence that is retro-inverso with respect to SEQ ID NO: 1, i.e. wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr. In one aspect of this preferred embodiment, at least one basic charged amino acid of said sequence is replaced with a different basic charged amino acid. In another aspect of this preferred embodiment, at least one acidic charged amino acid of said sequence is replaced with a different acidic charged amino acid. Advantageously, at least one non-polar amino acid of said sequence is replaced with a different non-polar amino acid. Preferably, at least one uncharged amino acid of said sequence is replaced with a different uncharged amino acid. In another aspect of this preferred embodiment, at least one aromatic amino acid of said sequence is replaced with a different aromatic amino acid. Advantageously, the peptide is modified at the amino terminus, carboxy terminus, or both amino and carboxy termini with a moiety independently selected from the group consisting of $CH_3CO$, $CH_3(CH_2)_nCO$, $C_6H_5CH_2CO$ and $H_2N(CH_2)_nCO$, wherein n=1–10. Preferably, the peptide is glycosylated. In another aspect of this preferred embodiment, one or more amide bonds of the peptide is reduced. Preferably, one or more nitrogens in said peptide is methylated. In still another aspect of this preferred embodiment, one or more carboxylic acid groups in the peptide is esterified. Preferably, the peptide consists of the amino acid sequence that is retro-inverso with respect to SEQ ID NO: 1, i.e. wherein said peptide consists of the sequence D-Pro-D-Ala-D-Cys-D-Leu-D-Lys-D-Glu-D-Val-D-Asn-D-Asn-D-Pro-D-Phe-D-Pro-D-Glu-Glv-D-Gln-D-Ala-D-Thr-D-Tyr.

Another embodiment of the invention is a composition comprising a retro-inverso peptide having between 18 and about 40 amino acids, wherein the peptide includes the sequence that is retro-inverso with respect to SEQ ID NO: 1, and a pharmaceutically acceptable carrier.

The present invention also provides a method for promoting neurite outgrowth or myelination in a mammal in need thereof, comprising the step of administering to the mammal an effective, neurite outgrowth or myelination facilitating amount of a composition comprising a retro-inverso peptide having between 18 and about 40 amino acids, wherein the peptide includes the sequence that is retro-inverso with respect to SEQ ID NO: 1, i.e. wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr. Preferably, the peptide has the amino acid sequence that is retro-inverso with respect to SEQ ID NO: 1, i.e. wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr. Advantageously, the mammal is a human. In one aspect of this preferred embodiment, the administering step is direct local injection, systemic, intracranial, intracerebrospinal, topical or oral.

Another embodiment of the invention is a retro-inverso peptide having between 18 and about 40 amino acids, wherein the peptide includes the sequence that is retro-inverso with respect to SEQ ID NO: 1 for use in promoting neurite outgrowth or myelination in a mammal in need thereof.

Preferably, the peptide has the amino acid sequence shown that is retro-inverso with respect to SEQ ID NO: 1. Advantageously, the mammal is a human.

The present invention also provides the use of a retro-inverso peptide having between 18 and about 40 amino acids, wherein the peptide includes the sequence that is retro-inverso with respect to SEQ ID NO: 1, i.e. wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr in the preparation of a medicament for promoting neurite outgrowth or myelination in a mammal in need thereof. Advantageously, the peptide of claim 5, wherein said peptide has the amino acid sequence that is retro-inverso with respect to SEQ ID NO: 1. Preferably, the mammal is a human.

DETAILED DESCRIPTION OF THE PREFERRED EMBODIMENTS

The present invention provides retro-inverso (RI) peptides derived from leukemia inhibitory factor (LIF) which mediate similar effects to native LIF, including regulation of growth and differentiation of osteoblasts and endothelial cells. The term "derived from" indicates that the peptides include the active region of interleukin-6, or analogs thereof as defined below. These RI LIF-derived peptides induce production by the liver of acute phase response proteins, support self renewal of cultured embryonic stem cells, inhibit lipogenesis, enhance survival of cultured motor neurons, and regulate growth and differentiation of osteoblasts and endothelial cells. The ability of a particular LIF-derived retro-inverso peptide to mediate an effect similar to the parent peptide can be determined by a person of ordinary skill in the art using standard LIF assays such as the one described in Example 10 below.

These RI LIF-derived peptides also have therapeutic applications in promoting functional recovery after toxic, traumatic, ischemic, degenerative and inherited lesions to the peripheral and central nervous system. These peptides are also useful in promoting increased myelination and for counteracting the effects of demyelinating diseases. The ability of any such peptide to stimulate neurite outgrowth and myelination, and to prevent neural cell death, can easily be determined by one of ordinary skill in the art using the procedures described in Examples 1–9 hereinbelow. The use of these peptides will facilitate treatment of various disorders since they will be more stable and easier to synthesize than either the native or recombinant cytokines.

A particular LIF-derived peptide, from which the retro-inverso peptide of the invention is based is shown in Table 1. The corresponding native (non-retro-inverted) peptides is disclosed in U.S. Pat. No. 5,700,909, the entire contents of which are hereby incorporated by reference.

TABLE 1

| Protein Name | sequence | SEQ ID NO: |
| --- | --- | --- |
| human LIF | YTAQGEPFPNNVEKLCAP | 1 |

As discussed above, these RI LIF-derived peptides have the same activities as the corresponding full-length LIF, and also possess neurotrophic and myelinotrophic activity. One embodiment of the present invention is a method of facilitating neurite outgrowth in differentiated or undifferentiated neural cells by administering to the cells an effective, neurite outgrowth-facilitating amount of a RI peptide having between 18 and about 40 amino acids, and encompassing the LIF-derived peptide that is retro-inverso with respect to SEQ ID NO: 1, or analogs thereof which have similar activity. Such analogs include, for example, replacement of one or more lysine and/or arginine residues with alanine or another amino acid; deletion of one or more lysine and/or arginine residues; replacement of one or more tyrosine and/or phenylalanine residues, deletion of one or more phenylalanine residues and conservative replacements of one or more amino acids within the peptide. The replacement or deletion of lysine/arginine and tyrosine/phenylalanine residues will reduce the susceptibility of peptide degradation by trypsin and chymotrypsin, respectively.

Additional variations of these peptide sequences contemplated for use in the present invention include minor insertions and deletions. Conservative amino acid replacements are contemplated. Such replacements are, for example, those that take place within a family of amino acids that are related in the chemical nature of their side chains. The families of amino acids include the basic charged amino acids (lysine, arginine, histidine); the acidic charged amino acids (aspartic acid, glutamic acid); the non-polar amino acids (alanine, glycine, valine, leucine, isoleucine, proline, phenylalanine, tryptophan); the uncharged polar amino acids (asparagine, glutamine, cysteine, methionine, serine, threonine, tyrosine); and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid will not have a major effect on the properties of the peptide. The ability of any RI peptide comprising the sequence that is retro-inverso with respect to the sequence shown in SEQ ID NO: 1, or insertions, deletions or substitutions thereof, to promote neurite outgrowth, myelination, reverse demyelination and prevent neural cell death can be determined using the assays provided in the examples presented below.

Various standard chemical modifications will improve the stability, bioactivity and ability of the peptide to cross the blood brain barrier. One such modification is aliphatic amino terminal modification with a derivative of an aliphatic or aromatic acid, forming an amide bond. Such derivatives include, for example, $CH_3CO$, $CH_3(CH_2)_nCO$ (n=1–10), $C_6H_5CH_2CO$, $H_2N-(CH_2)_nCO$ (n=1–10). Another modification is carboxy terminal modification with a derivative of an aliphatic or aromatic amine/alcohol coupled to the peptide via an amide/ester bond. Such derivatives include those listed above. The peptides may also have both amino and carboxy terminal modifications, wherein the derivatives are independently selected from those listed above. The peptides may also be glycosylated, wherein either the alpha amino group or a D-Asn, or both, are modified with glucose or galactose. In another contemplated modification, selected backbone amide bonds are reduced (—NH—CH$_2$). Other modifications include N-methylation of selected nitrogens in the amide bonds and esters in which at least one of the acid groups on the peptide are modified as aromatic or aliphatic esters. Any combination of the above modifications is also contemplated.

A typical minimum amount of the RI peptides of the invention for the LIF or neurotrophic activity in cell growth medium is usually at least about 5 ng/ml. This amount or more of the RI peptides of the invention for in vitro use is contemplated. Typically, concentrations in the range of 0.1 g/ml to about 10 g/ml of these peptides will be used. Effective amounts for any particular tissue can be determined in accordance with Example 1.

Cells can be treated in vitro or ex vivo by directly administering the RI peptides of the invention to the cells. This can be done, for example, by culturing the cells in growth medium suitable for the particular cell type followed by addition of the peptide to the medium. When the cells to be treated are in vivo, typically in a vertebrate, preferably a mammal, the composition can be administered by one of several techniques. Most preferably, the composition is injected directly into the blood in sufficient quantity to give the desired local concentration of peptide. These RI peptides persist longer in vivo due to the D peptide bonds. In the peptides lacking lysine and arginine residues, proteolytic degradation is reduced. The smaller peptides (i.e. 50-mer or less) will most likely cross the blood brain barrier and enter the central nervous system for treatment of CNS disorders (see Banks et al., Peptides, 13:1289–1294, 1992).

For treatment of neural disorders, direct intracranial injection or injection into the cerebrospinal fluid may also be used in sufficient quantities to give the desired local concentration of neurotrophin. In both cases, a pharmaceutically acceptable injectable carrier is used. Such carriers include, for example, phosphate buffered saline and Ringer's solution. Alternatively, the composition can be administered to peripheral neural tissue by direct local injection or by systemic administration. Various conventional modes of administration are contemplated including intravenous, pulmonary, intramuscular, intradermal, subcutaneous, intracranial, epidural, intrathecal, topical and oral.

The peptide compositions of the invention can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage. In a preferred embodiment, daily systemic dosages of the RI peptides of the invention based on the body weight of the vertebrate for promotion of LIF-induced processes, treatment of neurodegenerative diseases or demyelination diseases are in the range of from about 0.01 to about 10,000 g/kg. More preferably, daily systemic dosages are between about 0.1 and 1,000 g/kg. Most preferably, daily systemic dosages are between about 10 and 100 g/kg. Daily dosages of locally administered material will be about an order of magnitude less. Oral administration is particularly preferred because of the resistance of the peptides to proteolytic degradation in the gastrointestinal system.

In one preferred embodiment of the invention, the peptides are administered locally to neural cells in vivo by implantation thereof. For example, polylactic acid, polygalactic acid, regenerated collagen, multilamellar liposomes and many other conventional depot formulations comprise bioerodible or biodegradable materials that can be formulated with biologically active neurotrophic peptide compositions. These materials, when implanted, gradually break down and release the active material to the surrounding tissue. The use of bioerodible, biodegradable and other depot formulations is expressly contemplated in the present invention. Infusion pumps, matrix entrapment systems and combination with transdermal delivery devices are also contemplated. The peptides may also be encapsulated within a polyethylene glycol conformal coating as described in U.S. Pat. No. 5,529,914 prior to implantation.

The RI LIF-derived peptides of the invention may also be enclosed in micelles or liposomes. Liposome encapsulation technology is well known. Liposomes may be targeted to specific tissue, such as neural tissue, through the use of receptors, ligands or antibodies capable of binding the targeted tissue. The preparation of these formulations is well known in the art (Radin et al., Meth. Enzymol., 98:613–618, 1983).

There are currently no available pharmaceuticals able to promote full functional regeneration and restoration of the structural integrity of neural systems. This is particularly true of the CNS. Regeneration of peripheral nerves through the use of neurotrophic factors is within the scope of this invention. Moreover, neurotrophic factors can be therapeutically useful in the treatment of neurodegenerative diseases associated with the degeneration of neural populations or specific areas of the brain. The principal cause of Parkinson's disease is the degeneration of dopaminergic neurons of the substantia nigra. Since antibodies against prosaposin immunohistochemically stain the dopaminergic neurons of the substantia nigra in human brain sections, the RI peptides of the invention may be therapeutically useful in the treatment of Parkinson's disease. Retinal neuropathy, an ocular neurodegenerative disorder leading to loss of vision in the elderly, is also treatable using the RI peptides of the invention.

It has long been believed that in order to reach neuronal populations in the brain, neurotrophic factors would have to be administered intracerebrally since these proteins do not cross the blood brain barrier. U.S. Pat. No. 5,571,787 discloses that an iodinated neurotrophic 18-mer fragment derived from saposin C crosses the blood brain barrier. Thus, the RI peptides having up to about 22 amino acids will also cross this barrier and can thus be administered intravenously. Other neuronal populations, such as motor neurons, can also be treated by intravenous injection, although direct injection into the cerebrospinal fluid is also envisioned as an alternate route.

Cells may be treated to facilitate myelin formation or to prevent demyelination in the manner described above in vivo, ex vivo or in vitro. Diseases resulting in demyelination of nerve fibers including MS, acute disseminated leukoencephalitis, trauma to brain and/or spinal cord, progressive multifocal leukoencephalitis, metachromatic leukodystrophy, adrenal leukodystrophy and maldevelopment of the white matter in premature infants (periventricular leucomalacia) can be slowed or halted by administration of the neurotrophic peptides of the invention to the cells affected by the disease.

The RI LIF-derived peptide compositions of the present invention can also be used for supporting the self renewal of cultured embryonic stem cells, to enhance the survival of cultured motor neurons and for determining the effects of neurotrophic factors and myelin facilitating materials. However, more practically, they have an immediate use as laboratory reagents and components of cell growth media in order to facilitate growth and maintain neural cells and stem cells in vitro.

The peptides of the invention are synthesized using an automated solid-phase protocol well known in the art. All peptides are purified by high performance liquid chromatography (HPLC) to an extent greater than about 95% prior to use.

The following examples are merely illustrative and are not intended to limit the scope of the present invention.

EXAMPLE 1

Stimulation of Neurite Outgrowth

NS20Y neuroblastoma cells are grown in DMEM containing 10% fetal calf serum (FCS). Cells are removed with trypsin and plated in 30 mm petri dishes onto glass coverslips. After 20–24 hours, the medium is replaced with 2 ml DMEM containing 0.5% FCS plus 0, 0.5, 1, 2, 4 or 8 ng/ml of a RI peptide having between 18 and about 40 amino acids and including the sequence that is retro-inverso with respect to SEQ ID NO: 1. Cells were cultured for an additional 24 hours, washed with PBS and fixed with Bouin's solution (saturated aqueous picric acid/formalin/acetic acid 15:5:1) for 30 minutes. Fixative was removed with PBS and neurite outgrowth was scored under a phase contrast microscope. Cells exhibiting one or more clearly defined neurites equal to or longer than one cell diameter were scored as positive. At least 200 cells were scored in different portions of each dish to determine the percentage of neurite bearing cells and assays were performed in duplicate.

EXAMPLE 2

Prevention of Cell Death

NS20Y cells are plated as described in Example 1 and grown on glass coverslips in 0.5% fetal bovine serum for 2 days in the presence or absence of 8 ng/ml of an RI peptide having between 18 and about 40 amino acids and including the sequence that is retro-inverso with respect to SEQ ID NO: 1. Media is removed and 0.2% trypan blue in PBS is added to each well. Blue-staining dead cells are scored as a percentage of the total on an inverted microscope, counting 400 cells in four areas of each well. The average error of duplicates was 5%.

EXAMPLE 3

Promotion of Neurite Outgrowth Ex Vivo

Dorsal root ganglia are removed from adult rats and sensory neurons were prepared as described by Kuffler et al. (*J. Neurobiol.* 25:1267–1282, 1994). Neurons are treated with 0.5 ng/ml of an RI peptide having between 18 and about 40 amino acids and including the sequence that is retro-inverso with respect to SEQ ID NO: 1. After three days of treatment, the length of the longest neuritic projections was measured on a micrometer grid. The longest neurites in neurons treated with RI peptide are approximately three times longer than those treated with a control (non-RI) peptide or in untreated controls. After a 48 hour treatment, all cells respond similarly to nerve growth factor (NGF) in that extensive branching is observed. These results indicate that the LIF-derived peptides promote the differentiation of sensory neurons.

EXAMPLE 5

Reversal of Demyelination in a Rat Model

Experimental allergic encephalomyelitis (EAE) is a rat model of human multiple sclerosis (MS). In rats, EAE is induced by injecting foreign protein (guinea pig spinal cord) which results in inflammation and demyelination in white matter 11 days later. This demyelination resembles that seen in actively demyelinating human MS lesions (Liu et al., *Multiple Sclerosis* 1:2–9, 1995).

EAE is induced in Lewis rats by injection of an emulsion of guinea pig spinal cord and complete Freund's adjuvant (CFA). At day 14, when weakness is evident, treatment with RI peptides having between 18 and about 40 amino acids, and including the sequence that is retro-inverso with respect to SEQ ID NO: 1, is begun (200 g/kg intramuscularly) and continued for 8 days every day. Six rats are injected with vehicle only. Stride length, a measure of muscle weakness, is scored on days 14 and 22. In addition, the number and size of demyelinating lesions (plaques) in the spinal cord at day 22 per $mm^2$ is scored. Lastly, the amount of cholesterol ester in brain, a marker of myelin breakdown, is scored at day 22.

The stride length of both groups is decreased at day 14, whereas after treatment for 8 days, the LIF-derived peptide-treated animals return to normal, but the vehicle treated animals do not. A significant reduction of cholesterol ester content is observed in the brains of the treated group. Moreover, the number of spinal cord lesions is significantly reduced after 10 days of treatment with LIF-derived peptide. Lastly, the average lesion size is significantly reduced. There is no difference in weight loss between the control and experimental animals. These results indicate a significant clinical, biochemical and morphological reversal of EAE after systemic treatment with LIF-derived peptides. This action differs from the anti-inflammatory effect of current MS drugs which do not act directly upon myelin repair.

EXAMPLE 6

Ex Vivo Myelination Assay

Newborn mouse cerebellar explants are prepared according to Satomi (*Zool. Sci.* 9:127–137, 1992). Neurite outgrowth and myelination are observed for 22 days in culture, during the period when the newborn mouse cerebellum normally undergoes neuronal differentiation and myelination begins. An RI peptide having between 18 and about 40 amino acids, and including the sequence that is retro-inverso with respect to SEQ ID NO: 1, is added on the second day after preparation of the explants (three control and three treated explants) and outgrowth of neurites and myelination are assessed under a bright field microscope with a video camera. Saposin C is used as a positive control at a concentration of between about 1 and 10 g/ml. Myelination is stimulated by the LIF-derived peptides to a similar extent as with saposin C.

Alternatively, myelination may be assayed by incorporation of $^{35}S$ into sulfolipids which are exclusive to myelin as described below.

EXAMPLE 7

Incorporation of $^{35}S$ into Sulfolipids

Primary myelin-containing Schwann cells are incubated in low sulfate media (DMEM) containing 0.5% fetal bovine serum (FBS), followed by addition of $^{35}S$-methionine and an RI peptide having between 18 and about 40 amino acids, and including the sequence that is retro-inverso with respect to SEQ ID NO: 1, for 48 hours. Saposin C is used as a positive control. Cells are rinsed with PBS, harvested and sonicated in 100 1 distilled water. An aliquot of cell lysate is removed for protein analysis and the remainder is extracted with 5 ml chloroform/methanol (2:1, v/v). Lipid extracts are chromatographed and immunostained with anti-sulfatide monoclonal antibody as described (Hiraiwa et al., *Proc, Natl. Acad Sci U.S.A.* 94: 4778–4781). Similar amounts of sulfatide are observed after peptide and saposin C treatment.

EXAMPLE 8

Use of RI Peptides in Treating Traumatic Ischemic CNS Lesions

Humans with traumatic lesions to the brain or spinal cord receive systemic injections of about 100 g/kg of an RI peptide having between 18 and about 40 amino acids, and including the sequence that is retro-inverso with respect to SEQ ID NO: 1, in a sterile saline solution or in depot form. Improvement is assessed by gain of sensory or motor nerve function (i.e. increased limb movement). Treatments continue until no further improvement occurs.

EXAMPLE 9

Use of RI Peptides in Treating Demyelination Disorders

Patients diagnosed with early stage MS are given an RI peptide having between 18 and about 40 amino acids, and including the sequence that is retro-inverso with respect to SEQ ID NO: 1, by systemic injection using the same dose range as in Example 7. Dosages are repeated daily or weekly and improvement in muscle strength, musculoskeletal coordination and myelination (as determined by MRI) is observed. Patients with chronic relapsing MS are treated in the same manner when subsequent relapses occur.

EXAMPLE 10

LIF Cell Proliferation Assay

An RI peptide having between 18 and about 40 amino acids, and including the sequence that is retro-inverso with respect to SEQ ID NO: 1, is assayed for LIF activity by incubation with TF-1 cells (ATCC) in culture and measurement of TF-1 cell proliferation. TF-1 cells are human T cells whose proliferation in the presence of colony stimulating factor (CSF) is inhibited in response to LIF. TF-1 cells are washed 2 to 3 days after feeding and resuspended to a final concentration of $1 \times 10^6$ cells/ml in RPMI 1640 containing 5% FCS. Titrations of an LIF standard are distributed in 100 1 volumes in triplicate. The titration of the standard is started at 1 ng/ml and serial two-fold dilutions are made down to 0.1 pg/ml. Appropriate dilutions of the RI LIF peptides are made in 100 1 volumes in triplicate. Medium alone is included as a negative control. Cell suspension (100 1) is added to each well and plates are incubated for about 44 hours at 37 C in a humidified $CO_2$ incubator. Tritiated thymidine (0.5 Ci) is added to each well and plates are incubated for about 4 hours. The contents of each well are harvested onto filter mats and the amount of radiolabel is determined by liquid scintillation counting. A standard curve of absorbance versus concentration of standard is plotted. LIF activity of the RI LIF-derived peptides is estimated by comparison with the standard curve.

It should be noted that the present invention is not limited to only those embodiments described in the Detailed Description. Any embodiment which retains the spirit of the present invention should be considered to be within its scope. However, the invention is only limited by the scope of the following claims.

---

---

What is claimed is:

1. An isolated retro-inverso peptide having between 18 and about 40 amino acids, wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr.

2. The retro-inverso peptide of claim 1, wherein the peptide consists of the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr.

3. The retro-inverso peptide of claim 1, wherein said peptide is optionally modified, said modification selected from a group consisting of glycosylation, reduction of one or more amide bonds, methylation of one or more nitrogens, esterification of one or more carboxylic acid groups, and modification at the amino terminus, carboxy terminus, or both amino and carboxy termini with a moiety independently selected from the group consisting of $CH_3CO$, $CH_3(CH_2)_nCO$, $C_6H_5CH_2CO$ and $H_2N(CH_2)_nCO$, wherein n=1–10.

4. The retro-inverso peptide of claim 3, wherein the peptide consists of the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr.

5. A composition comprising a retro-inverso peptide having between 18 and about 40 amino acids, wherein said peptide comprises the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr.

6. The composition of claim 5, wherein said peptide consists of the sequence D-Pro-D-Ala-D-Cys-D-Leu-D-Lys-D-Glu-D-Val-D-Asn-D-Asn-D-Pro-D-Phe-D-Pro-D-Glu-Gly-D-Gln-D-Ala-D-Thr-D-Tyr.

7. A composition comprising the retro-inverso peptide of claim 1 and a pharmaceutically acceptable carrier.

8. A composition comprising the retro-inverso peptide of claim 3 and a pharmaceutically acceptable carrier.

9. A composition comprising the retro-inverso peptide of claim 4 and a pharmaceutically acceptable carrier.

* * * * *

UNITED STATES PATENT AND TRADEMARK OFFICE
CERTIFICATE OF CORRECTION

PATENT NO. : 7,109,168 B1
APPLICATION NO. : 10/048307
DATED : September 19, 2006
INVENTOR(S) : David E. Wright and D. Elliot Parks It is certified that error appears in the above-identified patent and that said Letters Patent is hereby corrected as shown below:

Column 1,
Lines 17-18, "cytok-ines" should read --cyto-kines--;
Lines 36-37, "macroph-ages" should read --macro-phages--.

Column 10,
Lines 59-60, "$CH_3$ $(CH_2)_nCO$" should appear on one line as --$CH_3(CH_2)_nCO$--.

Signed and Sealed this

Nineteenth Day of December, 2006

JON W. DUDAS
*Director of the United States Patent and Trademark Office*